United States Patent
Poxleitner et al.

(10) Patent No.: US 7,461,824 B2
(45) Date of Patent: Dec. 9, 2008

(54) STAND ARRANGEMENT FOR A MEDICAL-OPTICAL INSTRUMENT

(75) Inventors: Martin Poxleitner, Königsbronn (DE); Roland Brenner, Wallhausen (DE); Klaus Abele, Schwäbisch Gmünd (DE)

(73) Assignee: Carl Zeiss AG, Oberkochen (DE)

( * ) Notice: Subject to any disclaimer, the term of this patent is extended or adjusted under 35 U.S.C. 154(b) by 547 days.

(21) Appl. No.: 11/043,112

(22) Filed: Jan. 27, 2005

(65) Prior Publication Data

US 2005/0167550 A1  Aug. 4, 2005

(30) Foreign Application Priority Data

Jan. 29, 2004 (DE) .................. 10 2004 004 602

(51) Int. Cl.
  *E04G 3/00*  (2006.01)
(52) U.S. Cl. .............. 248/278.1; 248/123.11; 248/280.11; 248/364
(58) Field of Classification Search .......... 248/122.1, 248/123.11, 123.2, 125.7, 125.9, 280.1, 542, 248/648, 676, 364, 278.1, 280.11; 359/384, 359/382; 606/1, 102, 130
See application file for complete search history.

(56) References Cited

U.S. PATENT DOCUMENTS

| | | | | |
|---|---|---|---|---|
| 5,480,114 A | * | 1/1996 | Nakamura | 248/123.2 |
| 5,528,417 A | | 6/1996 | Nakamura | |
| 5,817,084 A | * | 10/1998 | Jensen | 606/1 |
| 6,406,472 B1 | * | 6/2002 | Jensen | 606/1 |
| 6,702,805 B1 | * | 3/2004 | Stuart | 606/1 |
| 2004/0190131 A1 | | 9/2004 | Brenner et al. | |

* cited by examiner

*Primary Examiner*—Korie H. Chan
(74) *Attorney, Agent, or Firm*—Walter Ottesen

(57) ABSTRACT

A stand arrangement (100) for a medical-optical instrument includes a first link (104) which is pivotally journalled on a holding unit (101) with a first rotational joint. The stand arrangement further includes a second link (107) which is rotatably connected to the first link (104) via a second rotational joint (106). In a forward section (108) of the second link (106), a take-up unit (110) for medical-optical equipment (111) is held with a third rotational joint (109). The take-up unit (110) includes a front link (112) which is coupled to a device for force transmission (115). This device is rotatably journalled on the second rotational joint (106). In the stand arrangement (100), a device is provided for coupling the holding unit and the device for force transmission. This device for coupling includes a flexible force transmitting element (133) which can be loaded in tension.

13 Claims, 6 Drawing Sheets

STAND ARRANGEMENT FOR A MEDICAL-OPTICAL INSTRUMENT

CROSS REFERENCE TO RELATED APPLICATION

This application claims priority of German patent application no. 10 2004 004 602.6, filed Jan. 29, 2004, the entire content of which is incorporated herein by reference.

FIELD OF THE INVENTION

The invention relates to a stand arrangement for a medical-optical instrument having a first link which is pivotally journalled with a first rotational joint on a holding unit. The stand arrangement further includes a second link, which is rotatably connected to the first link via a second rotational joint. In a forward section, the second link is connected to a third rotational joint which carries a take-up unit for medical-optical equipment. The take-up unit includes a front link coupled to a means for force transmission. This means for force transmission is rotatably journalled on the second rotatable joint. The stand arrangement further includes means for coupling the holding unit and the means for force transmission.

BACKGROUND OF THE INVENTION

A stand arrangement of this kind is known from U.S. Pat. No. 5,528,417. There, a stand arrangement for a medical-optical instrument is described which carries medical-optical equipment on a holding unit via first and second parallel linkage pairs. The medical-optical equipment is accommodated on a front link of a parallel linkage pair which is connected via a third linkage unit to a rotatably journalled device for force transmission in the form of a crank member. This crank member is coupled to the holding unit via a further rigid link unit. The crank member causes the front link to assume a specific orientation independently of the position of the first and second parallel linkage pairs in each position of the medical-optical equipment.

In U.S. patent application publication 2004/0190131 A1, a stand arrangement for a medical-optical instrument of the above-mentioned kind is described wherein a toothed gearing is provided for coupling the holding unit and the linkage-shaped configured means for force transmission.

SUMMARY OF THE INVENTION

It is an object of the invention to provide a stand arrangement for a medical-optical instrument of the kind described above wherein an orientation of the front link does not change independently of a position of a linkage unit.

The object of the invention is achieved with a stand arrangement wherein the means for coupling a holding unit and rotatably journalled means for force transmission have a mechanically flexible force transfer element which can be loaded in tension. Flexible force transmission elements, which can be loaded in tension, can be guided over suitable direction-changing elements in order to change the direction of forces. The direction-changing elements can, for example, be rollers. In this way, a space-saving configuration of the coupling means is made possible with simultaneously a comparatively low inherent weight.

The force transmission element can, for example, be configured as a cable, filament, belt or chain. Preferably, a cable and belt or chain is guided over a correspondingly adapted direction-changing roller or direction-changing sprocket. It is possible to rigidly connect a direction-changing roller or direction-changing sprocket to the holding unit. In this way, a direct force transmission from the holding unit to the means for force transmission is possible. However, it is also possible to rotatably journal the direction-changing roller or direction-changing sprocket on the holding unit. In this case, a brake device or a drive can, for example, be assigned to the direction-changing roller or direction-changing sprocket in order to make possible a vibration damping for the medical-optical instrument accommodated on the stand arrangement.

Preferably, a further link is provided for coupling the means for force transmission and the front link. This further link forms a first parallel linkage with the second link, the front link and the means for force transmission. Such a parallel linkage can be configured to be cropped in order to provide a large working space for an operating person who works with the medical-optical instrument accommodated on the stand arrangement.

In a further embodiment of the invention, the second link is extended in a rearward section in order to form a parallel linkage with two additional links on which parallel linkage at least one compensating weight is provided. In this way, it is possible to balance the stand arrangement.

In another embodiment of the invention, the holding unit is rotatable about an axis running essentially vertically. In this way, a three-dimensional movement for the medical-optical instrument, which is accommodated on the stand arrangement, is made possible.

In a further embodiment of the invention, the drive is connected to a control loop (open loop or closed loop). A vibration detector and/or an angle sensor and/or a distance sensor is assigned to the control loop for detecting a movement which is to be damped. In this way, vibrations of the medical-optical instrument, which is carried by the stand arrangement, can be actively compensated.

The holding unit and the means for force transmission can be so coupled that the orientation of the front link does not change when there is a movement of the first link or the second link. In this way, it is possible to introduce a torque into the front link by moving the medical-optical instrument on the take-up unit of the stand arrangement without this acting on an equilibrium state of the stand arrangement adjusted by means of the compensating weights.

The stand arrangement can be configured as a floor stand or a ceiling stand.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
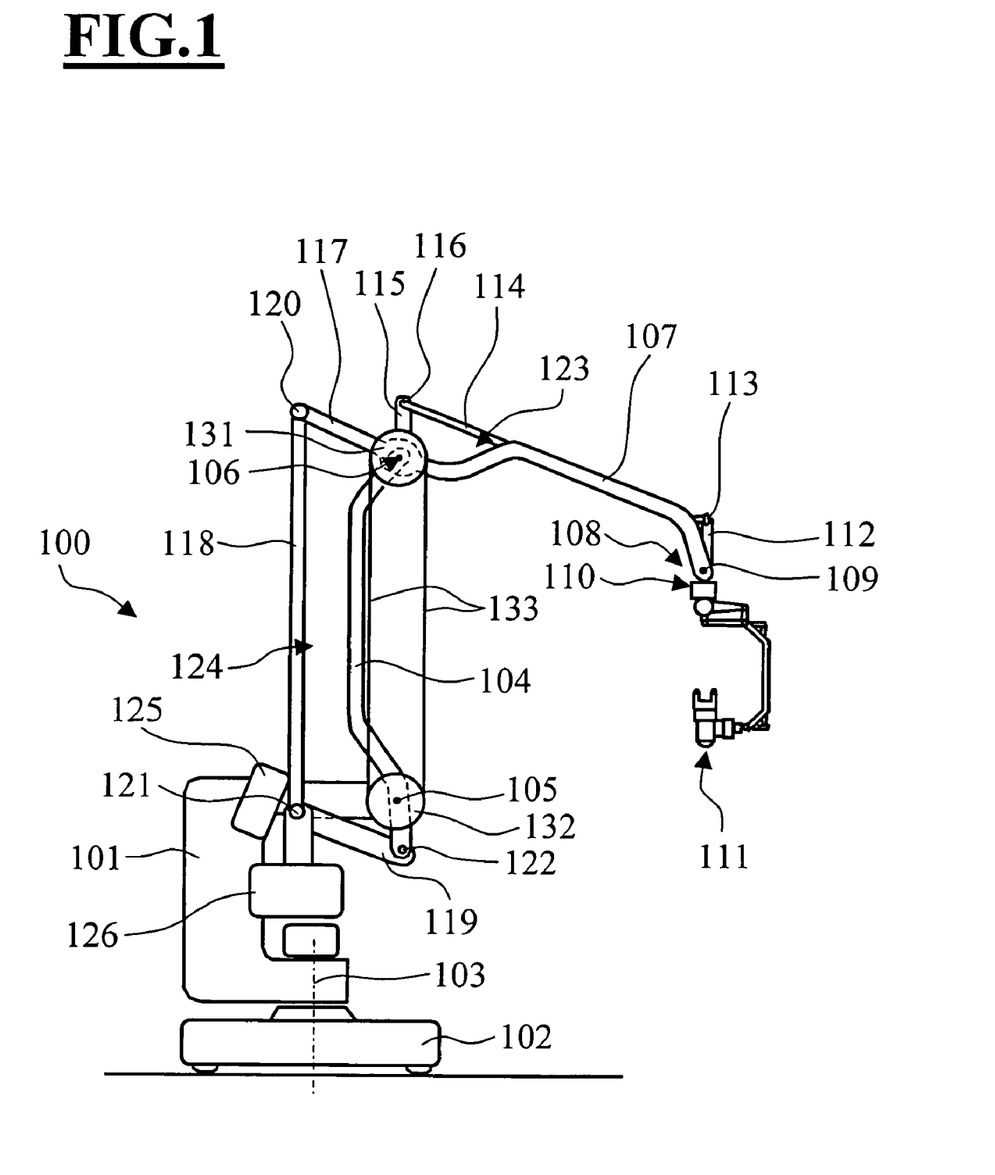
FIG. 1 shows a first embodiment of a stand arrangement of the invention.

FIG. 1 shows a stand arrangement 100 having a stand console 101 as a holding unit which is journalled on a stand base 102 by means of a rotary joint and can be moved about a rotational axis 103. A first link 104 is attached to the stand console 101 by means of a first rotational joint 105. A second link 107 is journalled on the first link 104 by a second rotational joint 106. A take-up unit 110 is held on a forward end 108 of the second link 107 by a rotational joint 109. This take-up unit 110 carries a surgical microscope 111 as medical-optical equipment. The take-up unit 110 includes a front link 112. This front link 112 is connected to a third link 114 via a joint 113. The link 114 is, in turn, connected to a fourth link 115 with a joint 116.

The link 115 is attached to the second rotational joint 106 so as to be pivotally movable. The link 115 functions as a means for transmitting forces to the front link 112. Link 115 and front link 112 are coupled to link 114 for this purpose.

The second link 107, the front link 112, the third link 114 and the fourth link 115 conjointly define a first parallel linkage 123. Compensating weights 125 and 126 are arranged on a second parallel linkage 124 in order to compensate for the weight of the surgical microscope 111 accommodated on the take-up unit 110.

The second link 107 is configured to be extended with an arm 117 at the end facing away from the take-up unit 110. A second parallel linkage 124 is formed by this second link 107 together with a sixth link element 118, a seventh link element 119, rotational joints (120, 121, 122) and rotational joint 106.

The fourth link 115 is rigidly connected to a direction-changing roller 131 whose center corresponds to the axis of the second rotational joint 106.

A direction-changing roller 132 is disposed on the holding unit 101. The center of the direction-changing roller 132 corresponds to the rotational axis of rotational joint 105. The direction-changing roller 132 is rigidly connected to the holding unit 101. The fourth link 115 is coupled to the holding unit 101 by a force transmission element in the form of a continuous cable 133. The force transmission element is flexible and can be loaded in tension and is placed over the direction-changing rollers 131 and 132. The cable 133 lies friction tight in cable guides formed on the direction-changing rollers 131 and 132. This coupling of the holding unit 101 and the fourth link 115 causes the orientation of the front link 112 to remain unchanged for movements of the first link 104 of the stand arrangement 100.

It is understood that a continuous filament can be used in lieu of the continuous cable 133.

Figure 2:
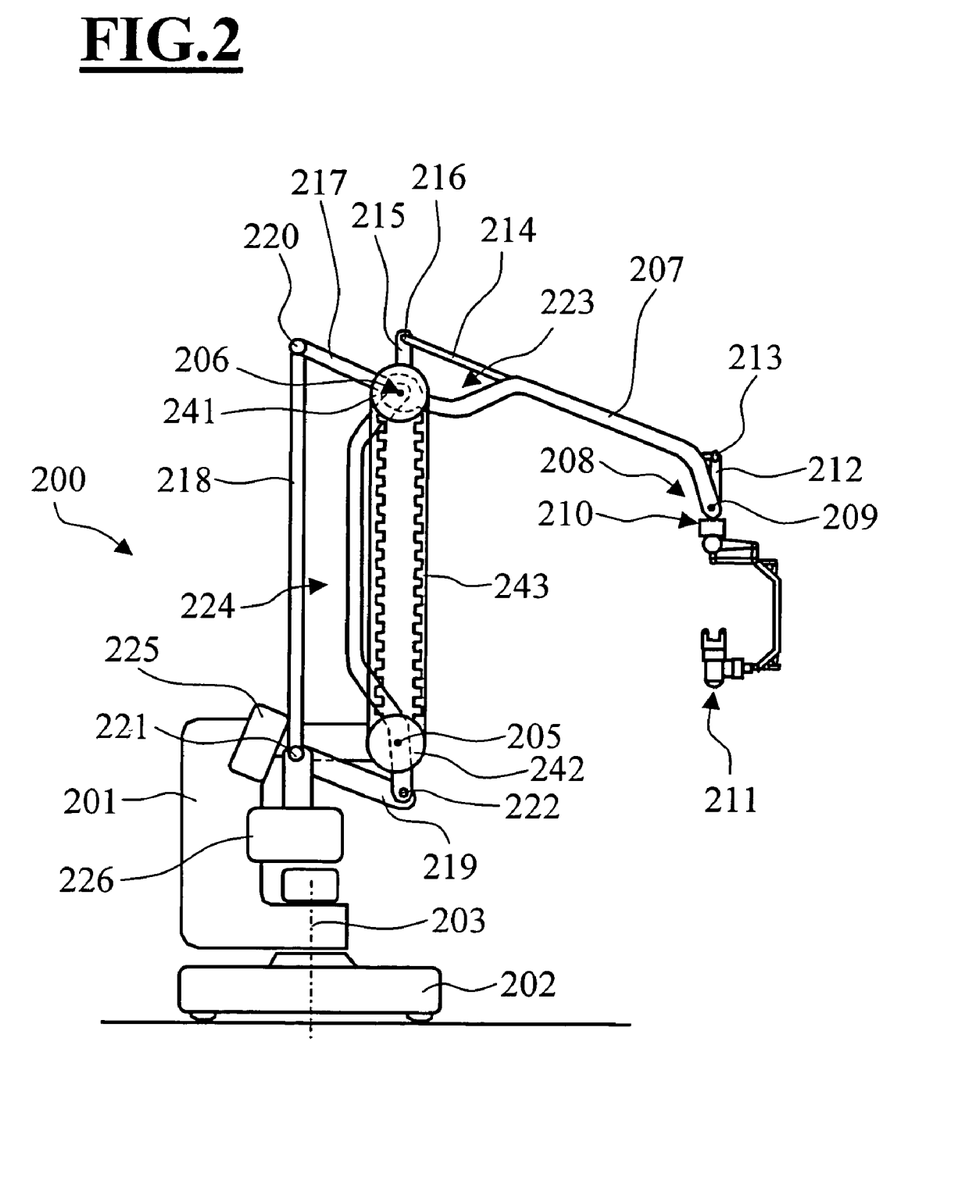
FIG. 2 shows a second embodiment of the stand arrangement of the invention.

FIG. 2 shows a stand arrangement 200 having a configuration corresponding essentially to that of the stand arrangement 100 of FIG. 1. Insofar as the stand arrangement 200 has component assemblies which are explained with respect to the stand arrangement 100, these components have reference numerals increased by 100.

The stand arrangement 200 differs from the stand arrangement 100 only in that a toothed belt 243 is provided for coupling the holding unit 201 and the fourth link 215. The toothed belt 243 is guided over correspondingly configured toothed-belt rollers 241 and 242 which correspond to the direction-changing rollers 131 and 132 of FIG. 1.

Figure 3:
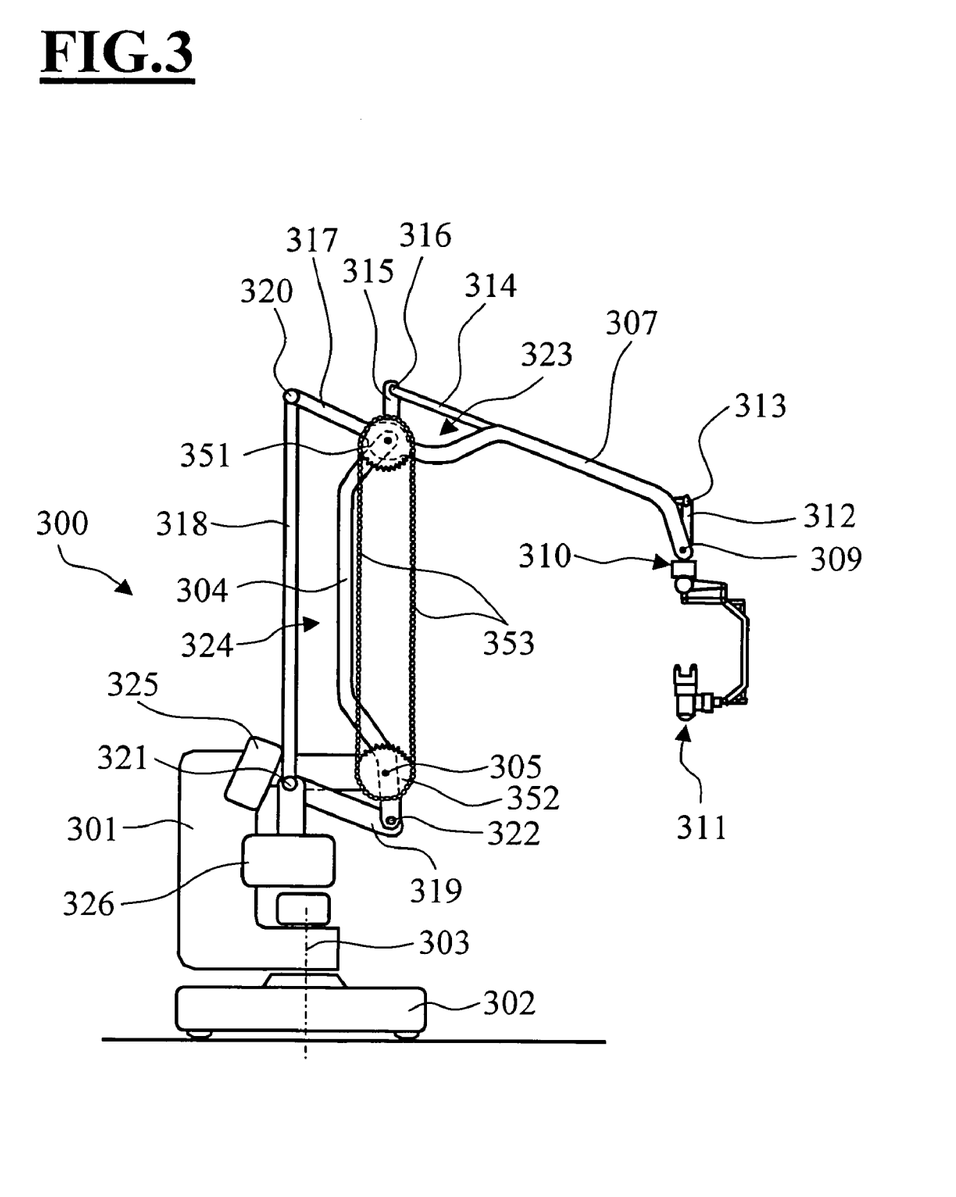
FIG. 3 shows a third embodiment of the stand arrangement of the invention.

FIG 3 shows a stand arrangement 300 wherein. compared to the stand arrangement 100 of FIG. 1, the direction-changing rollers and the continuous cable are replaced by a continuous chain 353 and corresponding sprockets 351 and 352. The configuration of the stand arrangement 300 corresponds to the stand arrangement 100 of FIG. 1. Component assemblies, which correspond to each other, have the same reference numerals as in FIG. 1 increased by 200.

Figure 4:
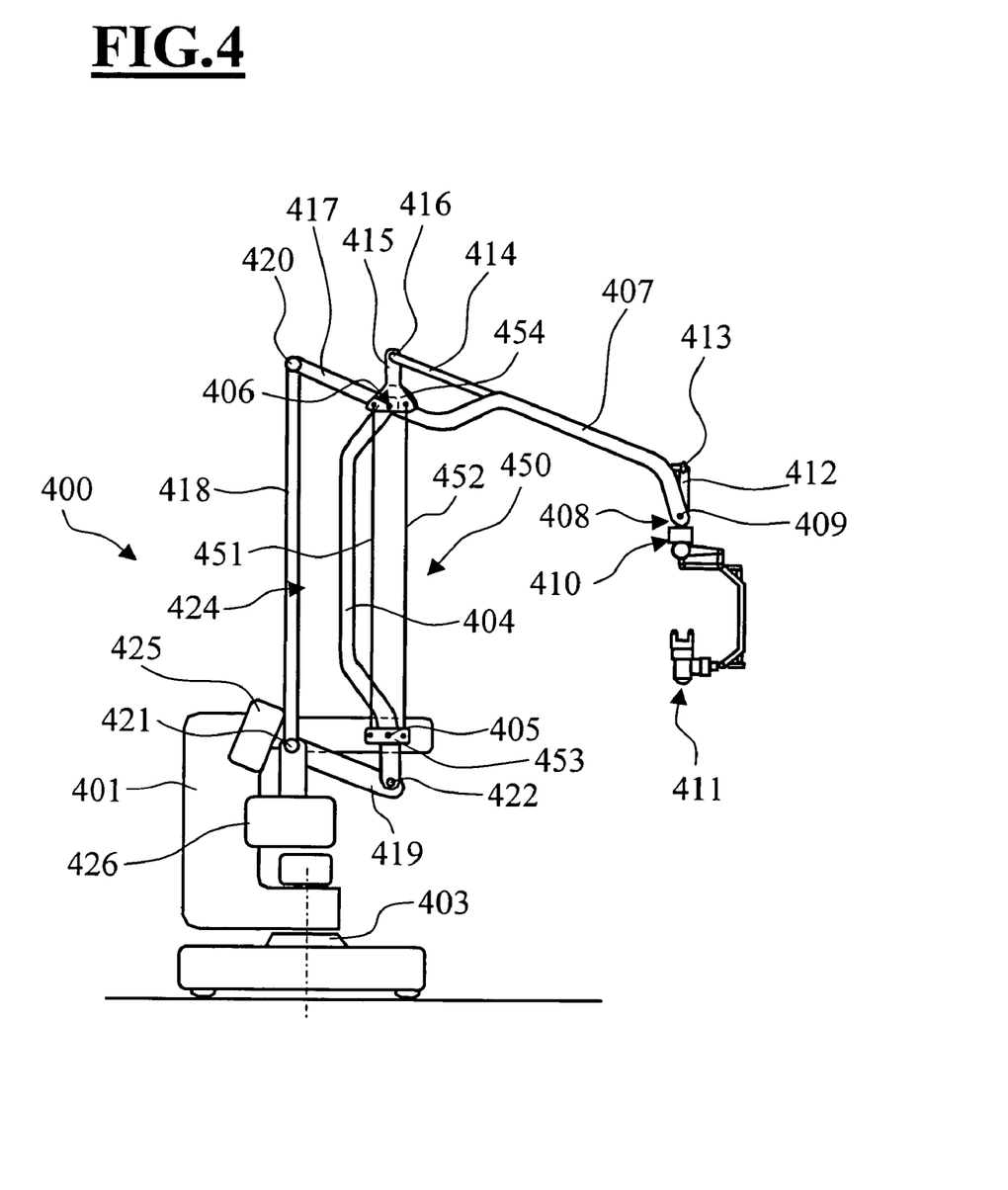
FIG. 4 shows a fourth embodiment of the stand arrangement of the invention.

FIG. 4 shows a stand arrangement 400 whose basic configuration corresponds to that of the stand arrangement 100 of FIG. 1. Insofar as the stand arrangement 400 has component assemblies, which have been explained with respect to FIG. 1, they carry reference numerals increased by 300 with respect to FIG. 1.

The stand arrangement 400 is different from that shown in FIG. 1 in that the link 415 is coupled to the holding unit 401 via a double cable construction 450. This double cable construction includes two individual cables 451 and 452 which connect a first crosspiece 453 and a second crosspiece 454. The first crosspiece 453 lies rigidly on the holding unit 401. The second crosspiece 454 is pivotally-movably journalled on the shaft of the rotational joint 406 and is simultaneously connected rigidly to the link 415.

It is noted that it is basically also possible in the stand arrangement 400 to assign a drive to the crosspiece 453 in order to, in this way, make possible an adjustment of the front link 412 or to make available an active vibration damping.

Figure 5:
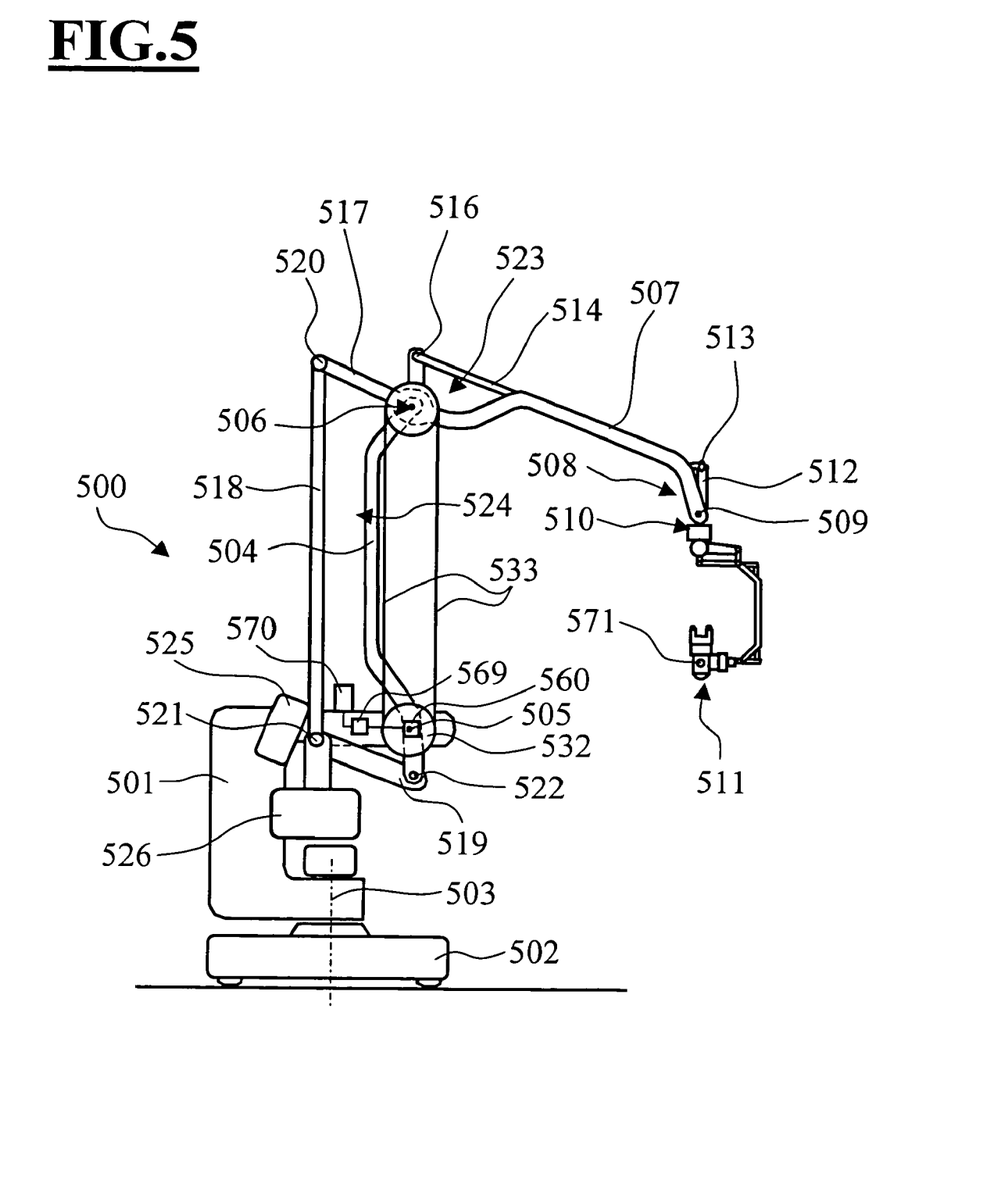
FIG. 5 shows a fifth embodiment of the stand arrangement of the invention.

FIG. 5 shows a stand arrangement 500 whose configuration corresponds also basically to that of stand arrangement 100 of FIG. 1. Here again, component assemblies are identified by the same reference numerals increased by 400 with respect to FIG. 1.

The stand arrangement 500 is different from the stand arrangement 100. The direction-changing roller 532 is rotatably journalled on the holding unit 501. A drive 560 is assigned to the direction-changing roller 532. This drive 560 makes it possible to adjust any desired orientation of the front link 512 by correspondingly shifting the direction-changing roller 532. It is noted that a shift of the front link 512 does not make it necessary to newly adjust the compensating weights 525 and 526 notwithstanding a displacement of a load accommodated on the take-up unit 510 in order to maintain the stand arrangement 500 in equilibrium. That means, in a settled equilibrium state, the front link 512 can be moved by driving the direction-changing roller 532.

To make an active damping decoupling possible, the drive can be connected via a switching element 569 optionally also to a control loop (open loop or closed loop) 570. A vibration detector 571 is assigned to this control loop 570 and is attached to the surgical microscope 511.

In this way, an active suppression of vibrations of the surgical microscope 511 is made possible on the stand arrangement 500.

In lieu of the continuous cable 533, it is noted that also a belt or a chain can be used in the embodiment of the stand arrangement of FIG. 5.

Figure 6:
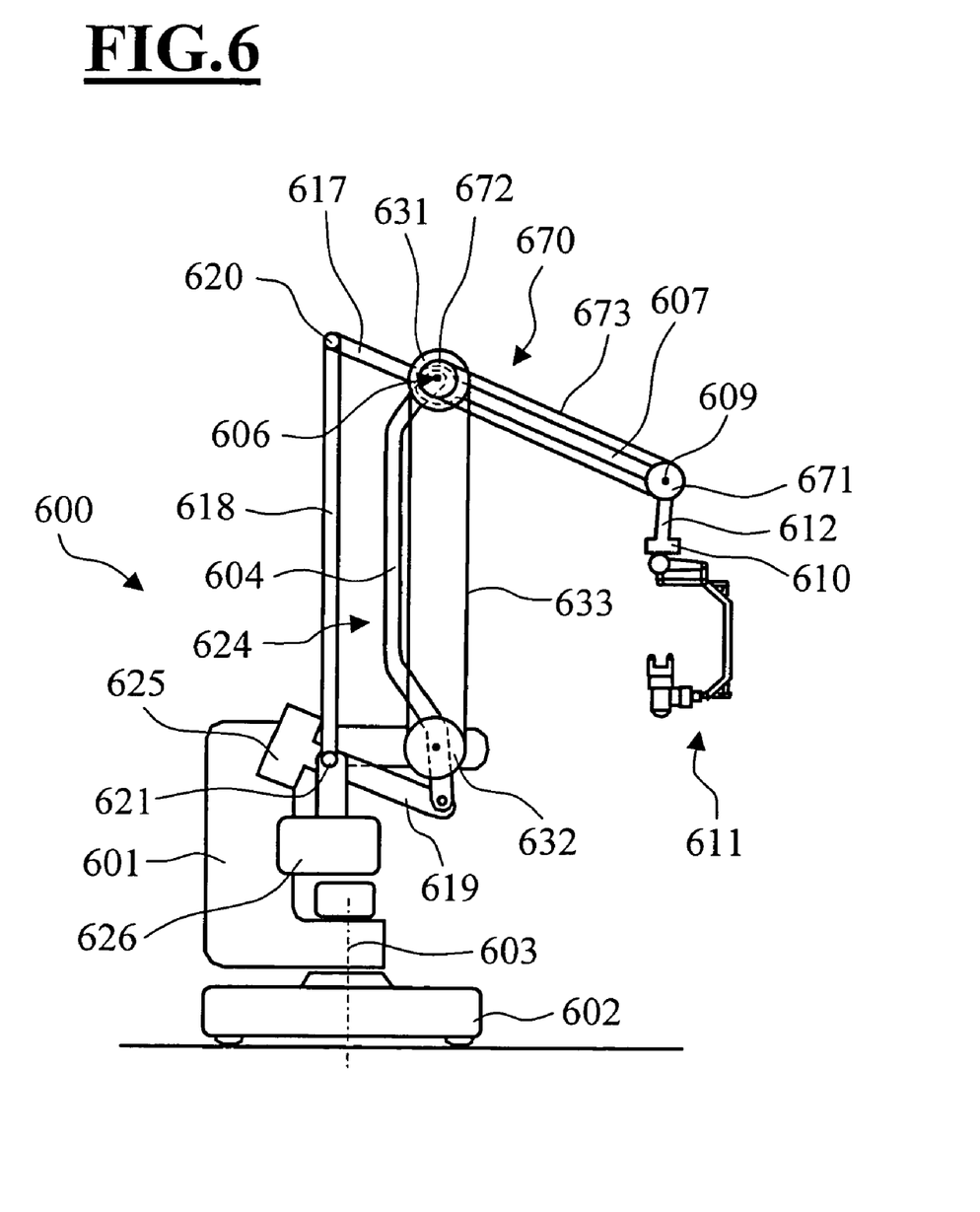
FIG. 6 shows a sixth embodiment of the stand arrangement of the invention.

FIG. 6 shows a stand arrangement 600 which corresponds basically to the configuration of the stand arrangement 100 of FIG. 1. The component assemblies of the stand arrangement 600, which are identical to the component assemblies of the stand arrangement 100 of FIG. 1, have the same reference numerals increased by 500.

Different than in the stand arrangement 100 of FIG. 1, a front link 612, which is rotatably journalled on a second link 607, is always aligned vertically via a further bowden cable mechanism 670. A take-up unit 610 is held with the surgical microscope 611 on the front link 612.

This bowden cable mechanism 670 includes a direction-changing roller 671 which is fixedly connected to the front link 612. The direction-changing roller 671 is coupled to a direction-changing roller 672 by means of a cable connection 673. The direction-changing roller 672 is disposed on the direction-changing roller 631 which is rotatably journalled in the rotational axis 606. The direction-changing roller 672 and the direction-changing roller 631 are fixedly connected to each other. As a consequence, the direction-changing roller 672 is coupled to the direction-changing roller 632 via the direction-changing roller 631 and the direction-changing cable 633. The direction-changing roller 632 is fixedly connected to the stand console 601. It is noted that, in lieu of the bowden cable mechanism 670, also a belt or chain mechanism can be provided as it is provided in FIG. 2 for coupling the direction-changing rollers 241 and 242 or the sprockets 351 and 352. Furthermore, it is possible to couple the front link 612 in FIG. 6 with a construction, which corresponds to the double cable construction 450 of FIG. 4, to a suitable means for force transmission in the form of a direction-changing roller 671 or the like.

Furthermore, it is noted that in mechanisms (which are explained with respect to FIGS. 1 to 6) for coupling a stand front link to a stand console, also such couplings can be adjusted which, for example, make possible an inclined alignment of the front link. With a movement of the link arrangement of the stand, the position of this front link does not change.

It is understood that the foregoing description is that of the preferred embodiments of the invention and that various changes and modifications may be made thereto without departing from the spirit and scope of the invention as defined in the appended claims.

What is claimed is:

1. A stand arrangement for a medical-optical instrument comprising:
   a holding unit;
   a first link;
   a first rotational joint for pivotally journalling said first link to said holding unit;
   a second link having a forward section;
   a second rotational joint for rotatably connecting said second link to said first link;
   a take-up unit for accommodating the medical-optical instrument;
   a third rotational joint disposed on said forward section;
   said second link carrying said take-up unit in said forward section via said third rotational joint;
   said take-up unit having a front link;
   a force transmitting device rotatably journalled on said second rotational joint;
   said front link being coupled to said force transmitting device;
   a coupling device for coupling said holding unit and said force transmitting device;
   said coupling device including a flexible force transmitting element which can be loaded in tension;
   said force-transmitting element being one of a cable, filament, belt and chain;
   said coupling device further including a first direction-changing roller and a second direction-changing roller; and, said cable or said belt being guided on said first and second direction-changing rollers; and,
   said first direction-changing roller being rotatably journalled on said holding unit.

2. The stand arrangement of claim 1, said coupling device further including a brake unit assigned to said first direction-changing roller.

3. The stand arrangement of claim 1, said coupling device further including a drive assigned to said first direction-changing roller.

4. The stand arrangement of claim 1, further comprising an additional link for coupling said force transmitting device and said front link.

5. The stand arrangement of claim 4, wherein said second link, said front link and said force transmitting device conjointly define a first parallel linkage.

6. The stand arrangement of claim 1, wherein said holding unit is rotatable about an axis which is essentially vertical.

7. The stand arrangement of claim 1, wherein said stand arrangement is adapted to be mounted on a floor.

8. The stand arrangement of claim 1, wherein said stand arrangement is adapted to be mounted on a ceiling.

9. A stand arrangement for a medical-optical instrument comprising:
   a holding unit;
   a first link;
   a first rotational joint for pivotally journalling said first link to said holding unit;
   a second link having a forward section;
   a second rotational joint for rotatably connecting said second link to said first link;
   a take-up unit for accommodating the medical-optical instrument;
   a third rotational joint disposed on said forward section;
   said second link carrying said take-up unit in said forward section via said third rotational joint;
   said take-up unit having a front link;
   a force transmitting device rotatably journalled on said second rotational joint;
   said front link being coupled to said force transmitting device;
   a coupling device for coupling said holding unit and said force transmitting device;
   said coupling device including a flexible force transmitting element which can be loaded in tension;
   said force-transmitting element being one of a cable, filament, belt and chain;
   said coupling device further including a first direction-changing roller and a second direction-changing roller; and, said cable or said belt being guided on said first and second direction-changing rollers; and,
   said second direction-changing roller being rigidly connected to said force transmitting device.

10. A stand arrangement for a medical-optical instrument comprising:
   a holding unit;
   a first link;
   a first rotational joint for pivotally journalling said first link to said holding unit;
   a second link having a forward section;
   a second rotational joint for rotatably connecting said second link to said first link;
   a take-up unit for accommodating the medical-optical instrument;
   a third rotational joint disposed on said forward section;
   said second link carrying said take-up unit in said forward section via said third rotational joint;
   said take-up unit having a front link;
   a force transmitting device rotatably journalled on said second rotational joint;
   said front link being coupled to said force transmitting device;
   a coupling device for coupling said holding unit and said force transmitting device;
   said coupling device including a flexible force transmitting element which can be loaded in tension;
   further comprising an additional link for coupling said force transmitting device and said front link;
   said second link, said front link and said force transmitting device conjointly defining a first parallel linkage; and,
   said second link has a rearward section extended to form an arm and said stand arrangement further comprising first and second ancillary links; and, said first and second ancillary links and said arm conjointly defining a second parallel linkage.

11. The stand arrangement of claim 10, further comprising at least one balancing weight on said second parallel linkage.

12. A stand arrangement for a medical-optical instrument comprising:
- a holding unit;
- a first link;
- a first rotational joint for pivotally journalling said first link to said holding unit;
- a second link having a forward section;
- a second rotational joint for rotatably connecting said second link to said first link;
- a take-up unit for accommodating the medical-optical instrument;
- a third rotational joint disposed on said forward section;
- said second link carrying said take-up unit in said forward section via said third rotational joint;
- said take-up unit having a front link;
- a force transmitting device rotatably journalled on said second rotational joint;
- said front link being coupled to said force transmitting device;
- a coupling device for coupling said holding unit and said force transmitting device;
- said coupling device including a flexible force transmitting element which can be loaded in tension;
- said force-transmitting element being one of a cable, filament. belt and chain;
- said coupling device further including a first direction-changing roller and a second direction-changing roller; and, said cable or said belt being guided on said first and second direction-changing rollers;
- said first direction-changing roller being rotatably journalled on said holding unit;
- said coupling device further including a drive assigned to said first direction-changing roller; and,
- a control loop connected to said drive; said control loop including sensor means for detecting a movement which is to be dampened; and, said sensor means being at least one of a vibration detector, an angle sensor and a distance sensor.

13. A stand arrangement for a medical-optical instrument comprising:
- a holding unit;
- a first link;
- a first rotational joint for pivotally journalling said first link to said holding unit;
- a second link having a forward section;
- a second rotational joint for rotatably connecting said second link to said first link;
- a take-up unit for accommodating the medical-optical instrument;
- a third rotational joint disposed on said forward section;
- said second link carrying said take-up unit in said forward section via said third rotational joint;
- said take-up unit having a front link;
- a force transmitting device rotatably journalled on said second rotational joint;
- said front link being coupled to said force transmitting device;
- a coupling device for coupling said holding unit and said force transmitting device;
- said coupling device including a flexible force transmitting element which can be loaded in tension; and,
- said holding unit and said force transmitting device being so coupled that the orientation of said front link does not change when there is a movement of said first link or said second link.

* * * * *

UNITED STATES PATENT AND TRADEMARK OFFICE
CERTIFICATE OF CORRECTION

| | | |
|---|---|---|
| PATENT NO. | : 7,461,824 B2 | Page 1 of 1 |
| APPLICATION NO. | : 11/043112 | |
| DATED | : December 9, 2008 | |
| INVENTOR(S) | : Martin Poxleitner, Roland Brenner and Klaus Abele | |

It is certified that error appears in the above-identified patent and that said Letters Patent is hereby corrected as shown below:

Column 3:
Line 54: delete "wherein." and substitute -- wherein, -- therefor.

Column 7:
Line 25: delete "ment." and substitute -- ment, -- therefor.

Signed and Sealed this

Third Day of March, 2009

JOHN DOLL
*Acting Director of the United States Patent and Trademark Office*